United States Patent [19]

Wunder et al.

[11] Patent Number: 4,481,376
[45] Date of Patent: Nov. 6, 1984

[54] PROCESS FOR THE SYNTHESIS OF LOWER OLEFINS FROM METHANOL AND/OR DIMETHYL ETHER

[75] Inventors: Friedrich Wunder, Flörsheim am Main; Ernst I. Leupold, Neu-Anspach; Heinz Litterer, Wiesbaden, all of Fed. Rep. of Germany

[73] Assignee: Hoechst Aktiengesellschaft, Frankfurt am Main, Fed. Rep. of Germany

[21] Appl. No.: 465,292

[22] Filed: Feb. 9, 1983

Related U.S. Application Data

[62] Division of Ser. No. 277,735, Jun. 26, 1981, abandoned.

[30] Foreign Application Priority Data

Jun. 28, 1980 [DE] Fed. Rep. of Germany ....... 3024536

[51] Int. Cl.$^3$ ................................................ C07C 1/20
[52] U.S. Cl. .................................... 585/640; 585/408; 585/469; 585/733; 502/242
[58] Field of Search .............. 585/640, 639, 408, 469, 585/733; 252/449, 455 Z; 502/249, 242

[56] References Cited

U.S. PATENT DOCUMENTS

| | | | |
|---|---|---|---|
| 3,006,909 | 10/1961 | Witt | 526/107 |
| 3,013,987 | 12/1961 | Castor et al. | 502/61 |
| 3,471,410 | 10/1969 | Oleck et al. | 502/65 |
| 3,528,768 | 9/1970 | Tucker | 423/328 |
| 3,804,747 | 4/1974 | Kimberlin et al. | 502/67 |
| 4,062,905 | 12/1977 | Chang et al. | 585/640 |
| 4,072,732 | 2/1978 | Hargis et al. | 585/639 |
| 4,247,731 | 1/1981 | Wunder et al. | 585/640 |
| 4,296,266 | 10/1981 | Wunder et al. | 585/640 |
| 4,358,397 | 11/1982 | Chu | 502/77 |
| 4,410,751 | 10/1983 | Shin et al. | 502/242 |

Primary Examiner—Delbert E. Gantz
Assistant Examiner—A. Pal
Attorney, Agent, or Firm—Curtis, Morris & Safford

[57] ABSTRACT

A method for the catalytic conversion of methanol and/or dimethyl ether to lower olefins with an aluminosilicate zeolite catalyst containing zirconium and/or hafnium together with manganese.

3 Claims, No Drawings

PROCESS FOR THE SYNTHESIS OF LOWER OLEFINS FROM METHANOL AND/OR DIMETHYL ETHER

This is a division of application Ser. No. 277,735 filed June 26, 1981, now abandoned.

Processes for the preparation of lower olefins from methanol and/or dimethyl ether on aluminum silicate catalysts are described in German Offenlegungsschrift No. 2,755,299, U.S. Pat. No. 4,062,905, 3,911,041, 4,079,096 and 3,979,472 and German Offenlegungsschrift No. 2,615,150. It is common to all these catalysts that they must periodically be regenerated, that is to say freed from by-products deposited on them; this can be effected by means of air at relatively low temperatures of 300° C. to 500° C.—most advantageously at the reaction temperature itself. Depending on the catalyst, this regeneration becomes necessary after varying intervals of time, the catalysts which have a high specific reactivity for lower olefins having relatively short operating times between regenerations, whereas the moderately non-specific catalysts which produce a broad range of gasoline hydrocarbons, aromatics and olefins often have longer operating times between regenerations. This has raised the problem of modifying the highly selective catalysts—which produce virtually only ethylene and propene—in such a way that they achieve a longer operating time between regenerations, which would considerably increase their profitable usefulness. Surprisingly, this can be achieved by adding a small quantity of hafnium ions and/or zirconium ions. Aluminum silicate catalysts containing hafnium and/or zirconium are active for a very much longer period and thus form considerably more ethylene and propene from methanol and/or dimethyl ether than do the same catalysts to which hafnium and/or zirconium have not been added. Since ethylene and propene are important raw materials for the chemical industry and are therefore considerably more valuable than gasoline, it is of particular interest to provide a highly selective catalyst exhibiting a stable and long catalyst life.

The invention relates to an aluminum silicate catalyst for the synthesis of lower olefins from methanol and/or dimethyl ether, which catalyst contains aluminum silicate and 0.1 to 10% by weight of hafnium or zirconium or both. The invention also relates to the preparation of a catalyst of this type. The catalyst preferably contains 0.5 to 5% by weight of hafnium or zirconium or both. The percentages relate to the total weight of the finished catalyst. Whereas known aluminum silicate catalysts for the conversion of methanol into lower olefins have an operating time of only a few hours before they have to be regenerated, particularly if they are highly active and highly selective, the operating time is extended to a very much longer period if hafnium and/or zirconium is added.

Examples of suitable starting materials for the catalyst according to the invention are natural or synthetic crystalline aluminum silicates, such as the molecular sieves which are known under the designations of faujasites, zeolites, chabasites, analcime, gismondite, gmelinite, natrolite, mordenites and erionites. It is advantageous to use the chabasite-erionite mixture which occurs naturally in large quantities. Furthermore, the conventional, amorphous acid cracking catalysts, which generally contain between 13 and 25% by weight of aluminum oxide and 75 to 87% by weight of silica, are also suitable.

In order to prepare the catalysts according to the invention, the aluminum silicates, either before or after—preferably after—being stabilized, for example by extraction by washing with ethylenediaminetetraacetic acid or by treatment with a silane compound, are laden with hafnium ions or zirconium ions in such a way that the finished catalyst contains 0.1–10% by weight, preferably 0.5–5% by weight, of hafnium and/or zirconium.

The hafnium or zirconium ions can be applied by impregnating the aluminum silicate with an appropriate quantity of a hafnium or zirconium salt or by partial ion exchange. In the case of impregnation with hafnium or zirconium salts, it is advantageous to have an aging period of a few days before the wet catalyst is dried. Suitable hafnium or zirconium salts are any soluble hafnium or zirconium salts, for example hafnium or zirconium oxychloride, oxybromide or oxysulfate, hafnium or zirconium oxalate, or hafnium or zirconium alkali metal carbonates. Water is generally used as the solvent. After being doped with zirconium or hafnium, the aluminum silicate is preferably additionally laden with manganese, in particular by means of ion exchange, but also, if appropriate, simply by impregnation with a manganese salt. In the event of such doping with manganese, the manganese content is generally 0.1 to 10% by weight. It effects an increase in the selectivity in favor of lower olefins.

Preferred solvents for the manganese salts are water, methanol, formamide, dimethylformamide or mixtures thereof, particularly water. Suitable manganese salts are any readily soluble and easily accessible salts, for example the formate, acetate, propionate, butyrate, lactate, citrate, tartrate, malate, chloride, bromide, nitrate or sulfate.

Furthermore, it has often proved advantageous for high selectivity to use, additionally, further elements as co-catalysts. Suitable elements of this type are those which exist in a monovalent, divalent or trivalent state in their compounds, such as, for example, the alkali metals (particularly lithium, sodium and potassium), the alkaline earth metals (particularly magnesium, calcium and barium), zinc, cadmium, lanthanum, rare earths (such as praseodymium, neodymium, samarium, gadolinium or mixtures thereof, such as didymium) and beryllium.

These metal ions which are active as co-catalysts can be applied jointly or successively; however, in the case of a common solution, it is necessary to take account of the mutual effect on solubility, that is to say, for example, if calcium or barium are used, sulfates are unsuitable.

Before, or immediately after, the application of hafnium and/or zirconium, the aluminum silicates are preferably stabilized by being washed with a solution of ethylenediaminetetraacetic acid or tartaric acid, the pH of which has been adjusted to pH 3–7, preferably to pH 4–5. Examples of suitable bases are lithium hydroxide, sodium hydroxide, potassium hydroxide, rubidium hydroxide and cesium hydroxide, particularly sodium hydroxide and potassium hydroxide. Alkali metal salts of weak acids, such as the carbonates, are also suitable.

The concentration of the solutions of ethylenediaminetetraacetic acid or tartaric acid can vary within wide limits, from an approx. 1% strength solution to a saturated solution; solutions which are approximately saturated at room temperature are preferred. The temperature of these solutions is preferably between 0° C. and 50° C. Preferred solvents are water, methanol, formamide, dimethylformamide or mixtures thereof, particularly water. After being extracted by washing with ethylenediaminetetraacetic acid solution or tartaric acid solution, the catalyst is washed with the solvent alone in order to remove the ethylenediaminetetraacetic acid or tartaric acid, respectively.

In the preparation of lower olefins from methanol using the catalyst according to the invention, it is possible either to pass methanol directly over the catalyst (and the methanol can contain a high proportion of water), or first to convert the methanol completely or partially into dimethyl ether and water on a customary dehydration catalyst, such as, for example, aluminum oxide or aluminum silicate, and then to pass the ether over the catalyst, on its own or together with the water which is present or has been formed and any unreacted methanol. However, it is also possible to use mixtures of methanol and dimethyl ether or dimethyl ether on its own as the starting material.

The feed components methanol and/or dimethyl ether can also be introduced into the reaction after dilution with inert gases. Hydrogen, nitrogen and carbon dioxide, for example, are suitable for reducing the partial pressure. However, this purpose can also be effected by carrying out the reaction under reduced pressure, down to 0.1 bar.

The water content of the feed materials can vary within wide limits, from anhydrous to about 80% of water, but larger quantities of water give rise to higher evaporation and distillation costs, so that the upper limit of the water content is determined by economic considerations.

The reaction temperature is generally between 300° C. and 500° C., preferably between 380° C. and 420° C. If the reaction conditions selected are such that only an incomplete conversion of methanol and/or dimethyl ether is achieved, the unreacted fractions can be separated off and recycled. The alkenes prepared on the catalysts according to the invention can be separated from the alkanes formed as by-products and from one another by the customary methods, for example by distillation.

A catalyst is thus provided which makes it possible to prepare lower alkenes of industrial importance from methanol and/or dimethyl ether in the presence of large quantities of water and in a particularly selective, and therefore economical; manner, the operating times of the catalyst between regenerations being many times longer than those of the conventional catalysts. The average space-time efficiency of these catalysts, which produce ethylene and propene in a highly specific manner, is thereby increased considerably.

The examples which follow illustrate the use of the catalyst according to the invention.

COMPARISON EXAMPLE 1

300 ml of a commercial chabasite-erionite mixture, in the form of extrudates, are covered with 300 ml of saturated aqueous manganese acetate solution and are extracted by washing with water after 48 hours and are dried. This gives 202 g of catalyst containing 3.6% by weight of manganese. 89.1 g per hour of methanol are passed over this catalyst at 1 bar and 400° C. This gives 25 l per hour of gas, of the following composition:
26.6% by weight of ethylene
27.9% by weight of propylene
4.6% by weight of butenes
6.7% by weight of methane
1.3% by weight of ethane
17.4% by weight of propane
3.0% by weight of butane
0.5% by weight of miscellaneous products
12.0% by weight of dimethyl ether, as well as 9.2 g/hour of methanol and 43.3 g/hour of water. This corresponds to an 89.6% conversion of methanol, a selectivity of conversion to $C_2$-$C_4$ olefins of 68.9% and a selectivity of conversion to $C_2$-$C_4$ hydrocarbons of 93%, if the dimethyl ether formed and the unreacted methanol are recycled. After 6 hours, the efficiency has declined while the selectivity has remained constant, and the proportion of dimethyl ether increases correspondingly.

COMPARISON EXAMPLE 2

Comparison Example 1 is repeated, with the sole difference that water is added to the feed methanol. A feed rate of 87.4 g per hour of methanol and 43.1 g per hour of water gives 26 l/hour of a gas containing:
30.0% by weight of ethylene
29.4% by weight of propene
5.4% by weight of butenes
7.3% by weight of methane
1.2% by weight of ethane
13.2% by weight of propane
2.2% by weight of butane
0.3% by weight of miscellaneous products
11.3% by weight of dimethyl ether, as well as 7.8 g/hour of methanol and 86.0 g/hour of water. This corresponds to a methanol conversion of 91.1%, a selectivity of conversion to $C_2$-$C_4$ olefins of 74.2% and a selectivity of conversion to $C_2$-$C_4$ hydrocarbons of 92.5%, if dimethyl ether and unreacted methanol are recycled. After 5 hours, the catalyst has to be regenerated owing to declining efficiency and it then regains the same efficiency as at the start.

EXAMPLE 1 (USING HAFNIUM)

200 g of a chabasite-erionite mixture bonded with 5% of alumina are covered with a saturated solution of the disodium salt of ethylenediaminetetraacetic acid and are allowed to stand for 48 hours, extracted by washing with distilled water and dried. 4 g of hafnium oxychloride hydrate ($HfOCl_2.8H_2O$) are then dissolved in 70 ml of water and the catalyst is impregnated with this solution, allowed to stand for 48 hours at room temperature and then dried. It is then impregnated with a solution of 9 g of manganese acetate hydrate in 75 ml of water and is dried. The finished catalyst contains 1% by weight of manganese and 1% by weight of hafnium.

320 ml per hour of 50:50 methanol/water are passed over this catalyst at 400° C. and 1 bar. This gives 37 l/hour of gas, of the following composition:
34.8% by weight of ethylene
33.2% by weight of propene
7.4% by weight of butenes
3.1% by weight of methane
0.9% by weight of ethane
4.6% by weight of propane
2.6% by weight of butane
1.9% by weight of miscellaneous products
11.5% by weight of dimethyl ether, as well as 222 g/hour of water and 5.7 g/hour of methanol.

This corresponds to a selectivity of conversion to ethylene of 40.2%,
to propene of 38.4% and
to butenes of 8.6%.

$C_2-C_4$ Olefins are formed at an overall selectivity of 87.2% and $C_2-C_4$ hydrocarbons at a selectivity of 96.5%, if the dimethyl ether is recycled.

The efficiency figures are virtually unaltered after an operating time of 8 hours.

EXAMPLE 2 (USING ZIRCONIUM)

210 g of a commercial chabasite-erionite mixture in the form of 1.5 mm extrudates are treated with a 10% strength solution of the disodium salt of ethylenediamine-tetraacetic acid and are extracted by washing with water and dried. 0.8 g of zirconyl chloride is then dissolved in 70 ml of water and the catalyst is impregnated with this solution and dried after a waiting time of 62 hours. It is then impregnated with a solution of 9.5 g of manganese acetate in 70 ml of water and is dried.

The finished catalyst contains 0.1% by weight of zirconium and 1% by weight of manganese.

300 ml per hour of a mixture composed of two parts by weight of methanol and one part by weight of water are passed over this catalyst at 400° C. and 1 bar.

In the course of one hour this gives 49 l of a gas of the following composition:
  36.1% by weight of ethylene,
  37.3% by weight of propene
  5.8% by weight of butenes
  2.5% by weight of methane
  0.9% by weight of ethane
  3.7% by weight of propane
  2.8% by weight of butane
  1.4% by weight of miscellaneous products
  9.5% by weight of dimethyl ether, as well as 181 g of water and 6.9 g of methanol; this corresponds to a selectivity of conversion to ethylene of 40%, to propene of 41.3% and to butenes of 6.4%, and a selectivity of conversion to $C_2-C_4$ olefins of 87.7% and to $C_2-C_4$ hydrocarbons of 97%.

After an operating time of 8 hours the ethylene efficiency has only declined negligibly.

EXAMPLE 3 (USING HAFNIUM)

210 g of a commercial chabasite-erionite mixture in the form of 1 mm extrudates are thoroughly washed with a 10% strength solution in water of disodium ethylene-diaminetetraacetic acid, rinsed with water and dried. This catalyst is covered with a saturated solution of hafnium oxychloride and, after 48 hours, is extracted by washing with water, dried and impregnated with a solution of 9 g of manganese acetate in 70 ml of water and subsequently dried. The finished catalyst contains 8.3% of hafnium and 1% of manganese.

300 ml per hour of a mixture composed of two parts of methanol and one part of water is passed over this catalyst at 400° C. and 1 bar.

In the course of one hour, this gives 51 l of a gas of the following composition:
  12.7% by weight of ethylene
  8.3% by weight of propene
  3.6% by weight of butenes
  1.8% by weight of methane
  0.8% by weight of ethane
  4.8% by weight of propane
  2.4% by weight of butane
  64.4% by weight of dimethyl ether
  1.2% by weight of miscellaneous products, as well as 147 g of water and 16.3 g of methanol.

This corresponds to a selectivity of conversion
to ethylene of 36.0%,
to propene of 23.5% and
to butenes of 10.2%.

The $C_2-C_4$ olefins are formed at a selectivity of conversion of 69.7% and the $C_2-C_4$ hydrocarbons at a selectivity of conversion of 92.6%, if the dimethyl ether is recycled.

These figures are virtually unchanged after an operating time of 8 hours.

We claim:

1. A method for the catalytic conversion of methanol, dimethyl ether, or a mixture thereof, to lower olefins, which comprises using an aluminosilicate zeolite catalyst having applied thereto from 0.1 to 10 percent, by weight of the finished catalyst, of ions of hafnium, zirconium, or both, and from 0.1 to 10 percent, by weight of the finished catalyst, of ions of manganese, whereby the life of the catalyst is extended.

2. A method as in claim 1 wherein said hafnium, zirconium, or both are applied in an amount from 0.5 to 5 percent, by weight of the finished catalyst.

3. A method as in claim 1 wherein said aluminosilicate zeolite catalyst is stabilized by treatment with an effective amount of ethylenediaminetetraacetic acid or a silane prior to application of said ions.

* * * * *